United States Patent [19]

Friedman et al.

[11] 4,330,274
[45] May 18, 1982

[54] LIGHTING SYSTEM FOR A DENTAL HANDPIECE

[76] Inventors: Joshua Friedman, 13 Fairfield Ct., Ridgefield, Conn. 06877; Maurice F. Zetena, Jr., 31 Lampost Dr., West Redding, Conn. 06896

[21] Appl. No.: 248,971

[22] Filed: Mar. 30, 1981

[51] Int. Cl.³ .............................................. A61C 3/00
[52] U.S. Cl. ...................................... 433/29; 362/804
[58] Field of Search ................. 433/29; 362/804, 253; 408/16

[56] References Cited

U.S. PATENT DOCUMENTS

| | | | |
|---|---|---|---|
| 2,539,828 | 1/1951 | Goldis et al. | 433/29 |
| 3,634,938 | 1/1972 | Hutchinson | 433/29 |
| 4,171,572 | 10/1979 | Nash | 433/29 |
| 4,230,453 | 10/1980 | Reimers | 433/29 |

FOREIGN PATENT DOCUMENTS 15659 9/1980 European Pat. Off. ............. 433/29

*Primary Examiner*—Robert Peshock
*Assistant Examiner*—John J. Wilson

[57] ABSTRACT

The lighting system comprises a lamp assembly including a conductive block having a plurality of longitudinal passageways extending from one end of the block adjacent the proximal end of the handpiece in a configuration matching the fluid transmitting conduit configuration extending from the handpiece and terminating at the opposite end of the block, means connecting said passageways at said opposite end to an air/water supply tubing, slidable means for removably coupling the lamp assembly to the handpiece, said block having a cavity for housing a miniature halogen lamp with the halogen lamp longitudinally seated in the cavity, means in said cavity for detachably engaging said lamp such that said lamp may be removed for replacement without disturbing the fluid interface between the block and the supply tubing, said lamp having a light transmitting end in close optical coupling with the proximal end of the handpiece, and wherein said slidable means includes an aperture in a predetermined location and means for engaging said block in a first position for enclosing the lamp assembly and in a second position for exposing the light transmitting end of the lamp through such aperture in the sliding means. In the second position the light generated by the bulb is directed into a fiber optic bundle removably attached to the handpiece.

6 Claims, 4 Drawing Figures

LIGHTING SYSTEM FOR A DENTAL HANDPIECE

This invention relates to a lighting system for use in combination with a fluid driven dental handpiece.

In the past dentists have traditionally used overhead operatory lights for directing light into the patient's oral cavity to facilitate examination and operative procedures in the dental office. The draw backs to exclusively relying on extra oral lighting are many. Extra oral light is easily blocked or obscured by the dentist when the dentist is holding an instrument inside the patient's mouth or when retracting the patient's cheek. This limits the available light impinging on the surface that the dentist wishes to treat or examine. The problem becomes more severe with the advent of high speed dental drills which cut at very high rates and require greater visual ability because of the rapidity with which these drills remove tooth structure. The problem is most acute in cases of posterior teeth, deep cavities or in cases where the patient's mouth cannot open wide enough to permit more than the dentist's drill itself to reach the desired area. Also, in childrens dentistry where the mouth opening is particularly small, the dentist will be forced to work by "feel" more than by vizualization, because the illumination from the extra oral light source is almost completely blocked by the drill and the dentist's hand. In addition, patients often move their heads during the course of operative drilling. When this happens the position of the overhead light must be constantly readjusted. Still another problem exists when the dentist wishes to inspect an already prepared tooth. With only an extraoral lighting system, the dentist must perform the separate procedure of replacing the drill and inserting a dental mirror into the patient's mouth to reflect extraoral light onto the viewing area.

Over the years various alternate solutions for illuminating a patient's mouth have been proposed. Initially, various lighting devices incorporating a small light bulb were developed as removable attachments for the dental handpiece. All of the earlier devices were bulky and when mounted on the handpiece would reduce the maneuverability of the handpiece. These devices were also susceptible to burning the dentist's hand if accidentally touched. To overcome such deficiences some manufacturers of dental handpieces offer a specially adapted model which incorporates a light pipe such as a glass or plastic rod within the body of the handpiece for transmitting light through the handpiece from any light source remote from the handpiece. One method of coupling a light source to the handpiece is through the use of a flexible bundle of optical fibers. The bundle of optical fibers is typically combined in a common tubular cable with the air/water supply line of a conventional instrument dental delivery system. The use of optical fibers has not proven very successful due to the tendency of the fiber strands to break during normal flexing of the air/water supply line. When this happens, there is a gradual diminishing of light from the output end. This is particularly true in the areas of the fiber tubing near the handpiece where the dentist is constantly moving the handpiece. An alternative arrangement to the use of optical fibers is to affix the remote light upon the rear or proximal end of the handpiece. A commercial system embodying this solution employs a removable cartridge enclosing a small lamp and a plurality of conduits. The cartridge is inserted between the handpiece and the air/water supply line with the conduits arranged to intercouple the air/water supply line to the water and exhaust tubes extending from the handpiece. Power is delivered to the lamp through electrical wires which are passed through the supply cable to the cartridge. To replace the lamp the entire cartridge must be replaced which requires the user to repeatedly make and break the air/water and electrical connections between the handpiece and the supply cable. Since air is delivered to the handpiece under pressure the use of a removable cartridge tends to establish leaks at the detachable air/water terminal connections as well as to contribute to corrosion at the electrical interface with the cartridge.

The dental handpiece lighting system of the present invention eliminates all the drawbacks of the prior art systems and is adaptable for use both with a dental handpiece incorporating a light transmitting pipe and a standard dental handpiece which does not possess an integral light transmitting member. Accordingly, the lighting system of the present invention is suitable for use with any dental handpiece.

The lighting system of the present invention also makes use of a small inexpensive and conventional lamp preferably a halogen lamp which is arranged to be readily replaced with the system otherwise remaining intact. This configuration provides a more reliable air/water coupling interface since it is permanently fixed. Moreover, the coupling between the halogen lamp and the handpiece increases the light transmitting efficiency by 30% over prior art designs. The lamp is electrically isolated from the mechanical members and the dental handpiece. Power is supplied to the lamp by means of control apparatus forming an integral part of the lighting system of the present invention. The control apparatus permits the dentist to selectively control the operation of the lamp in concert with, or independent of, operation of the dental drill. The lighting system of the present invention may also be operated manually or remotely.

Other advantages and objects of the present invention will become apparent from the following detailed description of the invention when read in conjunction with the accompanying drawings of which:

Figure 1:
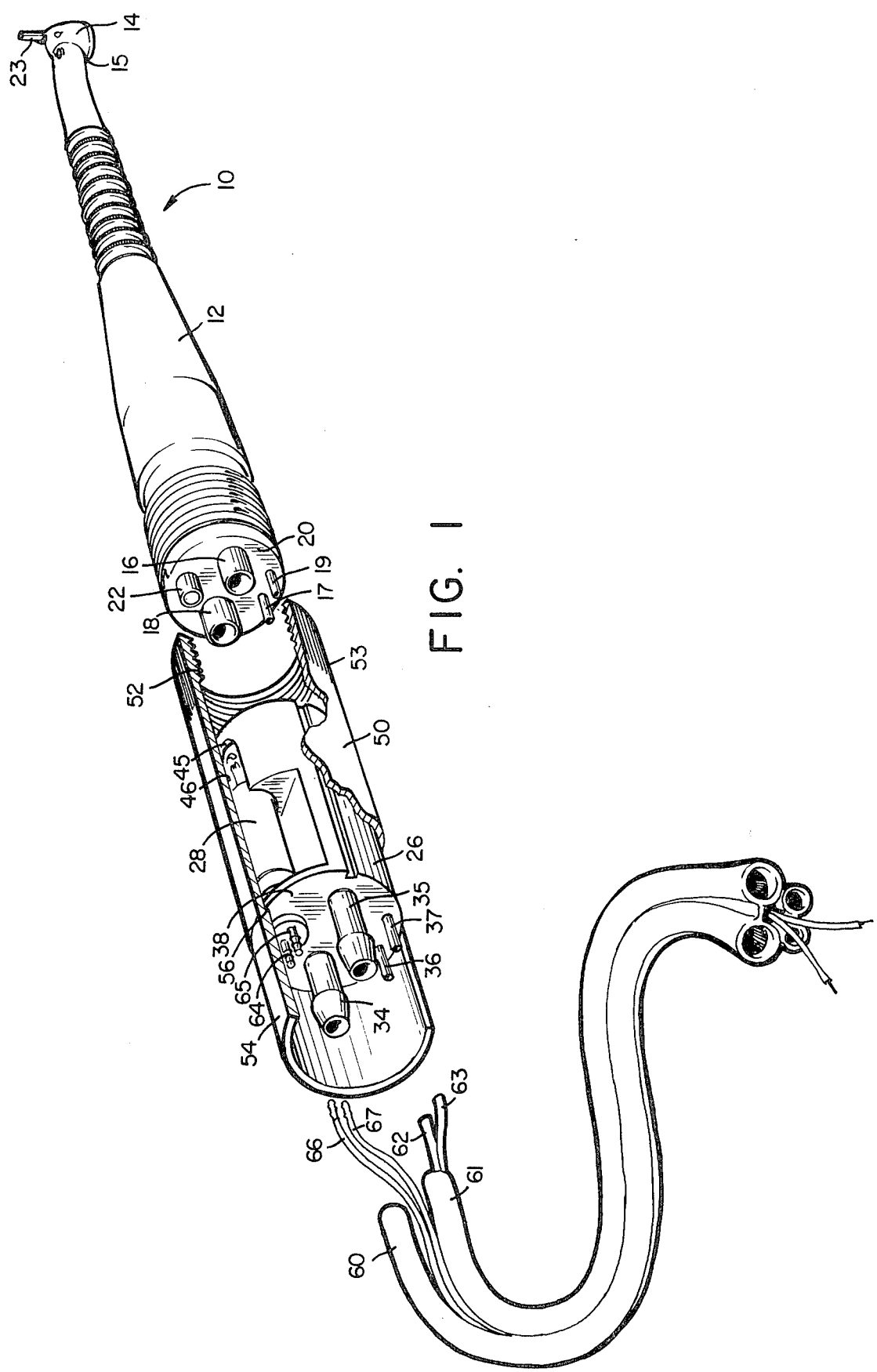
FIG. 1 is an exploded view in perspective of one embodiment of the lighting system lamp assembly of the present invention for use with a standard dental handpiece of the type having an internal light transmitting member.
Figure 2:
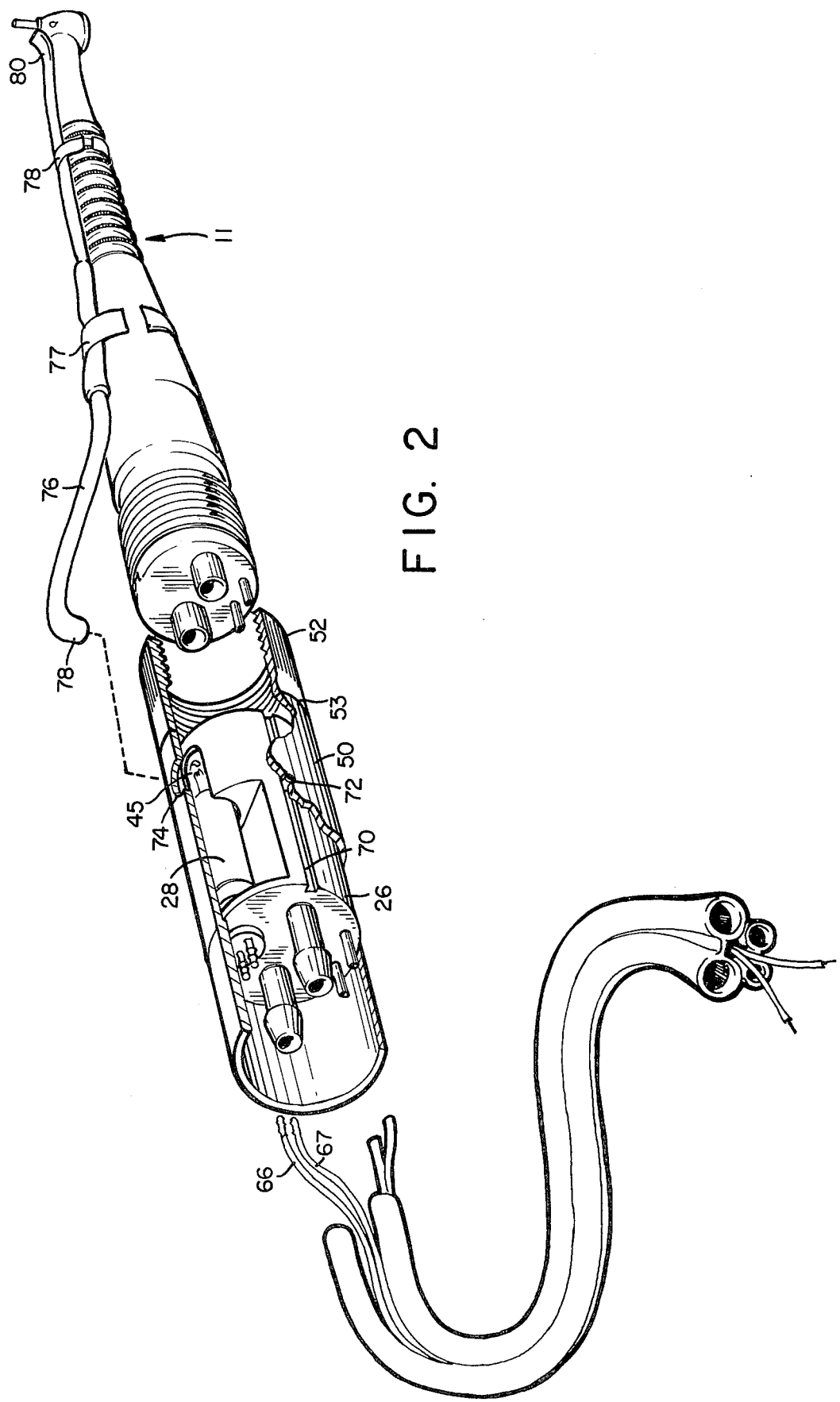
FIG. 2 is an exploded view in perspective of another embodiment of the lighting system lamp assembly of the present invention for use with a standard dental handpiece of the type without any internal light transmitting member.

The lighting system of the present invention comprises a lamp assembly and a control apparatus for delivering power to the lamp assembly under the operating control of the dentist. The lamp assembly may be used with a standard handpiece having an internal light transmitting member as depicted in FIG. 1 or with a standard dental handpiece without an integral light transmitting member as depicted in FIG. 2. The control apparatus, as will be explained hereafter in greater detail, is illustrated in the wiring diagram of FIG. 4 and may be integrated into a conventional dental delivering system or mounted separately for use in conjunction with an existing dental instrument delivery system.

Referring now to FIG. 1 in which a standard dental handpiece 10 is shown having a body 12, a turbine head 14 coupled to the operative end 15 of the body 12 and fluid transmitting conduits 16, 17, 18 and 19 extending from the rear or proximal end 20 of the handpiece 10. The handpiece 10 also includes a light transmitting fiber optic rod 22 extending from the proximal end 20 for transmitting light through the body 12 to the operative end 15 of the handpiece 10 where the fiber optic rod 22 exits in close proximity to the turbine head 14. The fiber optic rod 22 is preferably solid and of a glass or plastic composition. Any appropriate drill or bur may be affixed to the turbine head 14 to perform a desired dental operation such as drilling, cutting or polishing. The turbine head 14, as is shown in FIGS. 1 and 2, has a drill bit 23 secured therein.

Air enters and leaves the handpiece 10 through the fluid transmitting conduits 16 and 18 respectively. Water enters the handpiece through conduit 17 and is exhausted in a conventional manner through the head 14. Conduit 19 is used for the independent transfer of "Chip" air. The relative configuration between the fluid transmitting conduits 16, 17, 18 and 19 and the hole size of each conduit has now become standardized in accordance with the ISO configuration standards for dental handpieces. The disposition and diameter for the fiber optic rod 22 has also become standardized. The fiber optic rod 22 occupies a space at the proximal end 20 of the handpiece 10 which is otherwise unused in the standard configuration of FIG. 2 such that the fluid transmitting conduits 16, 17, 18 and 19 are in the same standardized configuration independent of the handpiece model selected.

The lamp assembly 24 includes a thermally conductive block 26 preferably of aluminum or thermally conductive plastic for housing a removable commercially available halogen lamp 28 of predetermined size. The block 26, which is preferably of a cylindrical geometry, is more clearly shown in FIG. 3 having a plurality of parallel passageways 29, 30, 31 and 32 extending longitudinally through the block 26. The passageways 29, 30, 31 and 32 terminate at the end face 33 of the block 26 in a hole size and configuration adapted for coupling to the air/water fluid conduits 16, 17, 18 and 19 extending from the handpiece 10. A plurality of tubes 34, 35, 36 and 37 are disposed in fluid sealed engagement with passageways 29, 30, 31 and 32 and extend from the opposite end face 38 of the block 26 in conformity with the handpiece configuration for the air/water fluid conduits 16, 17, 18 and 19 respectively.

Figure 3:
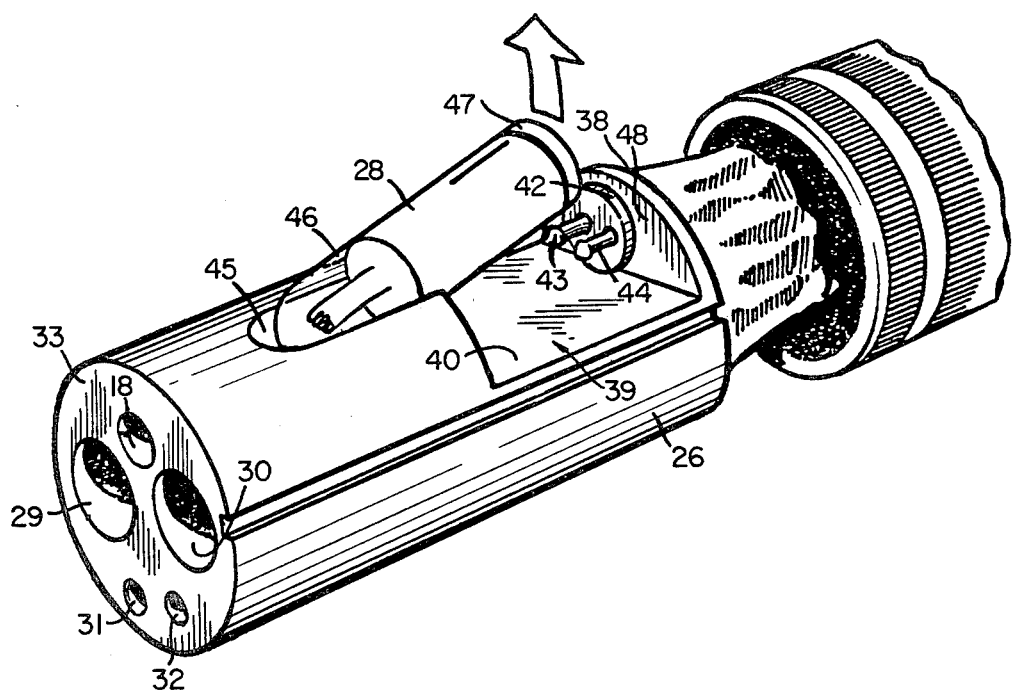
FIG. 3 is an enlarged perspective view of the lighting system lamp assembly of FIGS. 1 and 2.

The block 26 is partially cut away to form an open compartment 39 having a flat surface 40 and an upstanding wall 41 contiguous with the end face 38 of the block 26. An electrical socket 42 is mounted in the wall 41 with spring loaded electrical contacts 43, 44 extending into the open compartment 39. The electrical contacts 43, 44 are electrically isolated from the block 26 and shell 50. A slotted section 45 extends longitudinally from the open compartment 39 terminating just short of the end face 33 of block 26. The halogen lamp 28 is positioned to lie upon the flat surface 40 in the open compartment 39 with the light transmitting end 46 disposed in the slotted section 45 as shown in FIGS. 1 and 3 and with its base 47 held in detachable engagement against the spring loaded electrical contacts 43, 44. The slotted section 45 communicates through a short passageway 48 of less than 3 millimeters from the end face 33 of the block 26. The passageway 48 is aligned with the fiber optic rod 22 to provide a substantially close optical coupling between the halogen lamp 28 and the fiber optic rod 22.

A shell 50 surrounds the conductive block 26 for forming an enclosure for the lamp 28. The shell 50 is slidably adjustable over the block 26 with the forward end 52 threaded for engagement about the proximal end 20 of the handpiece 10. The shell 50 and the threaded end 52 are connected by a swivel joint coupling 53 of any conventional design which will permit the threaded end 52 to freely rotate relative to the shell 50. A conventional coupling is generally made using a captive nut secured to the shell by means of an expansion ring. The opposite end 54 of the shell 50 has a smaller internal diameter which acts as a stop upon engaging the end face 38 of the block 26.

The air conduits 34 and 35 extending from the end face 38 have barb ferrules which are adapted to be fixedly connected to corresponding supply tubes 60 and 61. Likewise the water conduit 36 and the chip air conduit 37 extending from the end face is adapted to be fixedly attached to the supply hoses 62 and 66 respectively. Also, the source of supply for the air and water supply hoses (not shown) is conventional. The electrical contacts 64, 65 extending from the electrical socket 41 are electrically connected to leads 66 and 67.

FIG. 2 is another embodiment of the lamp assembly 24 wherein like numerals are used to represent the counterparts of identical elements of FIG. 1. This lamp assembly is intended for use with a standard handpiece 11 which does not have an internal fiber optic rod. The block 26 includes a keyway or channel 70 in which a locking pin 72 is engaged. The keyway is provided on one side or symmetrically on two sides of the block 26. The locking pin 72 extends from the shell 50 to establish a predetermined special orientation for the shell 50 about the block 26. With the shell 50 in the locked position as shown in FIG. 2 an opening 74 in the shell 50 is automatically placed in a predetermined position above the light transmitting portion 45 of the halogen lamp 28. With the locking pin 72 rotated to engage the keyway on the opposite side of the block 26 the aperture 74 is hidden such as in the application of FIG. 1. A flexible fiber optic bundle 76 is detachably connected to the handpiece 11 by removable clips 77 and 78 which may be of any springy material preferably of corrosion resistant composition. The fiber optic bundle 76 has one end 78 fitted into the opening 74 in close optical coupling to the halogen lamp 28 for receiving light generated by the lamp filament. The fiber optic bundle 76 should have a bend 80 to position the light transmitting end 81 in approximate alignment with the drill bit 23.

Figure 4:
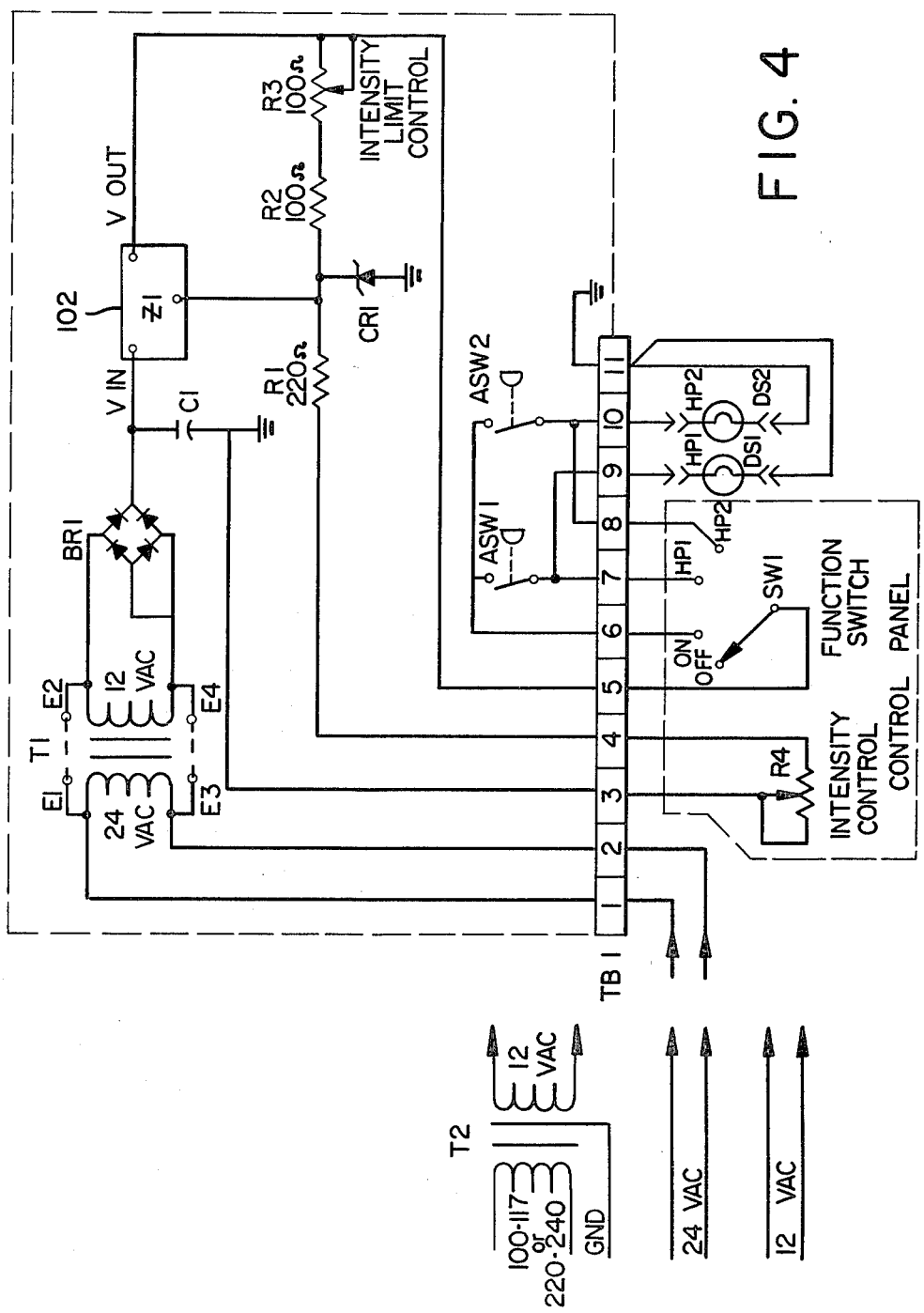
FIG. 4 is a schematic wiring diagram of the lighting system control apparatus of the present invention.

The control system for supplying power to the electrical leads 66 and 67 for energizing the lamp 28 is shown in FIG. 4. Power may be provided from any conventional source of alternating line voltage through an appropriate step down transformer T1 or T2 depending on the input voltage. Twenty-four volts AC is dropped to 12 volts AC through transformer T1. The 12 volt output across the secondary winding of transformer T1 is rectified to a DC source of power through a full wave diode bridge rectifier BRI. Electrolytic capacitor C1 acts as a filter to reduce AC ripple. The full wave rectified output Vin from the bridge rectifier is applied to a conventional voltage regulator circuit 102 such as for example, a V-LM 317 from National Semiconductor. The output Vout of the voltage regulator 102 is applied to an adjustable resistor divider network composed of resistors R1,R2,R3 and R4. Resistor R3 is an adjustable trimpot to assure proper voltage to either one of the handpiece lamp combinations denoted by HPI, DSI, HP2, and DS2 respectively. Each handpiece and lamp combination may be represented by either standard handpiece 10 or 11 of FIGS. 1 or 2 in combination with the lamp assembly 24. The maximum brightness is provided by varying the intensity control R4. Zener diode CR1 is a voltage limiter maintaining required ground reference to assure that a proper voltage is applied across either handpiece-lamp combination HPI, DSI or HP2, DS2 respectively in the event either terminal lead to resistor R4 is accidentally opened.

When the function switch SW1 is in the "on" position, the regulated voltage is applied to the two air switches ASW1 and ASW2 through the terminal block interconnection of terminal block positions 5 and 6. The switches ASW1 and ASW2 are operated automatically in response to air pressure from the dental instrument delivery system (not shown). In a conventional "drive air" delivery system the air switches ASW1 and ASW2 would be normally open in the absence of air pressure and closed or turned on when air pressure is applied during handpiece operation. Accordingly, for a drive air system with the function switch SW1 in the on position both handpiece lamps DS1 and DS2 are allowed to turn on. In a conventional pilot air delivery system the air pressure switches ASW1 and ASW2 are normally closed and switch open in the presence of air pressure from pilot air control system in the dental instrument delivery system (not shown). When each respective handpiece is removed from the hanger in which it is manually held, the air pressure drops which closes the air pressure switch corresponding to the removed handpiece, thereby turning on the respective lamp DS1 or DS2.

By rotating function switch SW1 to either the HP1 or HP2 positions, handpiece HP1 or handpiece HP2 is turned on through interconnection of terminal block position 5 to terminal block position 7 or 8 respectively. In either the HP1 or HP2 position the air circuit is bypassed thus providing an override mode of operation. The override mode can be used for transillumination where bur rotation is undesirable or when continuous light is required when operating in the drive air mode regardless of air pressure. It should be noted that foot control pedal switches (not shown) may be used in place of or in conjunction with the air switches. The function and intensity controls can be incorporated in a separate control panel module which may be remotely connected from the terminal block.

In addition, electrical switches which are mounted in mechanical linkage with the dental handpiece hangers may also be used to remotely control the lamps DS1 or DS2 by connecting these switches to positions 5, 7 and 8 of the terminal block in place of the rotary switch SW1.

What is claimed is:

1. A lighting system for use in combination with a fluid driven dental handpiece having a proximal end with fluid transmitting conduits extending therefrom in a standardized configuration, said lighting system comprising:
    a lamp assembly including a thermally conductive block having a plurality of longitudinal passageways extending from one end of the block in an arrangement for coupling to the fluid transmitting conduits of said handpiece and terminating at the opposite end of the block;
    conduit means extending from said passageways at the opposite end of said block for engagement with a plurality of air/water supply lines;
    slidable means for removably coupling the lamp assembly to the handpiece;
    said block having a cavity for housing a miniature halogen lamp with the halogen lamp being longitudinally seated in said cavity;
    means in said cavity for detachably engaging said lamp such that said lamp may be removed for replacement without disturbing the fluid interface between the block and the supply tubing;
    said halogen lamp having a light transmitting end disposed in close proximity to said one end of said block for adjoining a predetermined position at the proximal end of said handpiece, and having a base at the opposite end adapted for connection to a source of power; and
    wherein said slidable means includes an aperture in a predetermined location and means for engaging said block in a first position for enclosing said lamp assembly and in a second position for exposing the light transmitting end of the lamp through said aperture.

2. A lighting system as defined in claim 1 in which the dental handpiece includes an internal light transmitting member extending from the proximal end of the handpiece to the operative end thereof, with the light transmitting end of said lamp being in close optical coupling to said light transmitting member in said handpiece upon connecting said handpiece to said lamp assembly.

3. A lighting system as defined in claim 2 wherein said slidable means is a movable shell surrounding said block with said shell rotated to engage said block such that said aperture is disposed in an oriented position contiguous with said block and away from the light transmitting end of said lamp.

4. A lighting system as defined in claim 1 wherein said lamp assembly further comprises an elongated light transmitting member, means for removably attaching said light transmitting member to the body of said handpiece such that said member extends from a predetermined position adjacent the proximal end thereof to the operative end of the handpiece, with said slidable means being engaged to said block in said second position such that said aperture lies coterminous with the predetermined position of said light transmitting member.

5. A lighting system as defined in claims 2 or 4 further comprising a control assembly for supplying power to the halogen lamp in said lamp assembly, said control assembly including a transformer having a primary winding adapted to be connected to an alternating source of line potential and a secondary winding, rectifier means coupled to said secondary winding, air switch means having an open position responsive to the absence of air flow therethrough from a source of air supply and a closed position responsive to the presence of air flow from a source of air supply, manual switch means having a first position for operatively connecting the output from said rectifier means in an electrical series circuit relationship with said air switch means and said halogen lamp of said lamp assembly and a second position for bypassing said air switch means and directly connecting the output from said rectifier means in series circuit relationship with the halogen lamp of said lamp assembly.

6. A lighting system defined in claim 4 wherein said light transmitting member is a flexible fiber optic conduit.

* * * * *